United States Patent
Gaster et al.

(10) Patent No.: US 6,906,089 B2
(45) Date of Patent: Jun. 14, 2005

(54) TRIARYLIMIDAZOLE DERIVATIVES AS CYTOKINE INHIBITORS

(75) Inventors: Laramie Mary Gaster, Harlow (GB); John David Harling, Harlow (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/239,815

(22) PCT Filed: Mar. 26, 2001

(86) PCT No.: PCT/GB01/01314

§ 371 (c)(1), (2), (4) Date: Jan. 21, 2003

(87) PCT Pub. No.: WO01/72737

PCT Pub. Date: Oct. 4, 2001

(65) Prior Publication Data

US 2003/0149277 A1 Aug. 7, 2003

(30) Foreign Application Priority Data

Mar. 27, 2000 (GB) .............................. 0007405

(51) Int. Cl.[7] .................. A61K 31/443; A61K 31/4436; A61K 31/4439; C07D 401/04; C07D 405/04

(52) U.S. Cl. .................. 514/341; 514/341; 514/342; 514/343; 546/268.7; 546/269.4; 546/272.7; 546/280.4; 546/283.4

(58) Field of Search ............... 546/268.7, 269.4, 546/276.4, 272.7, 280.4, 283.4, 274.1; 514/341, 342, 343

(56) References Cited

U.S. PATENT DOCUMENTS 5,955,480 A    9/1999  Chang ................ 514/341

FOREIGN PATENT DOCUMENTS

| GB | 1 381 031 | 1/1975 |
|----|-----------|--------|
| JP | A11 180 958 | 7/1999 |
| WO | WO9314081 | 7/1993 |
| WO | WO9821957 | 5/1998 |
| WO | WO0061576 | 10/1999 |

OTHER PUBLICATIONS

Inman, Gareth J. et al, "SB–431542 is a Potent and Specific Inhibitor of TGF–b Superfamily Type I ALK Receptors ALK4, ALK5, & ALK7," Molecular Pharmacology (2002), vol. 62 (1), pp. 65–74.*

* cited by examiner

*Primary Examiner*—Ceila Chang
*Assistant Examiner*—Janet L. Coppins
(74) *Attorney, Agent, or Firm*—Nora Stein-Fernandez; Theodore R. Furman

(57) ABSTRACT

Compounds of formula (I) or a pharmaceutically acceptable salt thereof:

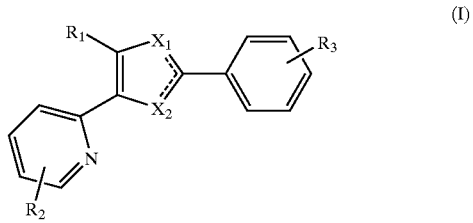

(I)

wherein $R_1$, $R_2$ and $R_3$ are various substituent groups; and one of $X_1$ and $X_2$ is N or CR", and the other is NR" or CHR" wherein R" is hydrogen, OH, $C_{1-6}$alkyl, or $C_{3-7}$cycloalkyl; or when one of $X_1$ and $X_2$ is N or CR" then the other may be S or O;

and their use as pharmaceuticals.

9 Claims, No Drawings

TRIARYLIMIDAZOLE DERIVATIVES AS CYTOKINE INHIBITORS

This invention relates to pyridyl substituted triarylimidazoles which are inhibitors of the transforming growth factor, ("TGF")-β signaling pathway, in particular, the phosphorylation of smad2 or smad3 by the TGF-β type I or activin-like kinase ("ALK")-5 receptor, methods for their preparation and their use in medicine, specifically in the treatment and prevention of a disease state mediated by this pathway.

TGF-β1 is the prototypic member of a family of cytokines including the TGF-βs, activins, inhibins, bone morphogenetic proteins and Müllerian-inhibiting substance, that signal through a family of single transmembrane serine/threonine kinase receptors. These receptors can be divided in two classes, the type I or activin like kinase (ALK) receptors and type II receptors. The ALK receptors are distinguished from the type II receptors in that the ALK receptors (a) lack the serine/threonine rich intracellular tail, (b) possess serine/threonine kinase domains that are very homologous between type I receptors, and (c) share a common sequence motif called the GS domain, consisting of a region rich in glycine and serine residues. The GS domain is at the amino terminal end of the intracellular kinase domain and is critical for activation by the type II receptor. Several studies have shown that TGF-β signaling requires both the ALK and type II receptors. Specifically, the type II receptor phosphorylates the GS domain of the type I receptor for TGFβ, ALK5, in the presence of TGF-β. The ALK5, in turn, phosphorylates the cytoplasmic proteins smad2 and smad3 at two carboxy terminal serines. Generally it is believed that in many species, the type II receptors regulate cell proliferation and the type I receptors regulate matrix production. Therefore, preferred compounds of this invention are selective in that they inhibit the type I receptor and thus matrix production, and not the type II receptor mediated proliferation.

Activation of the TGF-β1 axis and expansion of extracellular matrix are early and persistent contributors to the development and progression of chronic renal disease and vascular disease. Border W. A., Noble N. A., *N. Engl. J. Med.*, Nov. 10, 1994; 331(19):1286–92. Further, TGF-β1 plays a role in the formation of fibronectin and plasminogen activator inhibitor-1, components of sclerotic deposits, through the action of smad3 phosphorylation by the TGF-β1 receptor ALK5. Zhang Y., Feng X. H., Derynck R., *Nature*, Aug. 27, 1998; 394(6696):909–13; Usui T., Takase M., Kaji Y., Suzuki K., Ishida K., Tsuru T., Miyata K., Kawabata M., Yamashita H., *Invest. Ophthalmol. Vis. Sci.*, October 1998; 39(11):1981–9.

Progressive fibrosis in the kidney and cardiovascular system is a major cause of suffering and death and an important contributor to the cost of health care. TGF-β1 has been implicated in many renal fibrotic disorders. Border W. A., Noble N. A., *N. Engl. J. Med.*, Nov. 10, 1994; 331(19): 1286–92. TGF-β1 is elevated in acute and chronic glomerulonephritis, Yoshioka K., Takemura T., Murakami K., Okada M., Hino S., Miyamoto H., Maki S., *Lab. Invest.*, February 1993; 68(2):154–63, diabetic nephropathy, Yamamoto, T., Nakamura, T., Noble, N. A., Ruoslahti, E., Border, W. A., (1993) *PNAS* 90:1814–1818, allograft rejection, HIV nephropathy and angiotensin-induced nephropathy, Border W. A., Noble N. A., *N. Engl. J. Med.*, Nov. 10, 1994; 331(19):1286–92. In these diseases the levels of TGF-β1 expression coincide with the production of extracellular matrix. Three lines of evidence suggest a causal relationship between TGF-β1 and the production of matrix. First, normal glomeruli, inesangial cells and non-renal cells can be induced to produce extracellular-matrix protein and inhibit protease activity by exogenous TGF-β1 in vitro. Second, neutralizing anti-bodies against TGF-β1 can prevent the accumulation of extracellular matrix in nephritic rats. Third, TGF-β1 transgenic mice or in vivo transfection of the TGF-β1 gene into normal rat kidneys resulted in the rapid development of glomerulosclerosis. Kopp J. B., Factor V. M., Mozes M., Nagy P., Sanderson N., Bottinger E. P., Klotman P. E., Thorgeirsson S. S., *Lab Invest*, June 1996; 74(6):991–1003. Thus, inhibition of TGF-β1 activity is indicated as a therapeutic intervention in chronic renal disease.

TGF-β1 and its receptors are increased in injured blood vessels and are indicated in neointima formation following balloon angioplasty, Saltis J., Agrotis A., Bobik A., *Clin Exp Pharmacol Physiol*, March 1996; 23(3):193–200. In addition TGF-β1 is a potent stimulator of smooth muscle cell ("SMC") migration in vitro and migration of SMC in the arterial wall is a contributing factor in the pathogenesis of atherosclerosis and restenosis. Moreover, in multivariate analysis of the endothelial cell products against total cholesterol, TGF-β receptor ALK5 correlated with total cholesterol (P<0.001) Blann A. D., Wang J. M., Wilson P. B., Kumar S., *Atherosclerosis*, February 1996; 120(1–2):221–6. Furthermore, SMC derived from human atherosclerotic lesions have an increased ALK5/TGF-β type II receptor ratio. Because TGF-β1 is over-expressed in fibroproliferative vascular lesions, receptor-variant cells would be allowed to grow in a slow, but uncontrolled fashion, while overproducing extracellular matrix components McCaffrey T. A., Consigli S., Du B., Falcone D. J., Sanborn T. A., Spokojny A. M., Bush H. L., Jr., *J Clin Invest*, December 1995; 96(6):2667–75. TGF-β1 was immunolocalized to non-foamy macrophages in atherosclerotic lesions where active matrix synthesis occurs, suggesting that non-foamy macrophages may participate in modulating matrix gene expression in atherosclerotic remodeling via a TGF-β-dependent mechanism. Therefore, inhibiting the action of TGF-β1 on ALK5 is also indicated in atherosclerosis and restenosis.

TGF-β is also indicated in wound repair. Neutralizing antibodies to TGFβ1 have been used in a number of models to illustrate that inhibition of TGFβ1 signaling is beneficial in restoring function after injury by limiting excessive scar formation during the healing process. For example, neutralizing antibodies to TGF-β1 and TGF-β2 reduced scar formation and improved the cytoarchitecture of the neodermis by reducing the number of monocytes and macrophages as well as decreasing dermal fibronectin and collagen deposition in rats Shah M., *J. Cell. Sci.*, 1995, 108, 985–1002. Moreover, TGF-β antibodies also improve healing of corneal wounds in rabbits Moller-Pedersen T., *Curr. Eye Res.*, 1998, 17, 736–747, and accelerate wound healing of gastric ulcers in the rat, Ernst H., *Gut*, 1996, 39, 172–175. These data strongly suggest that limiting the activity of TGF-β would be beneficial in many tissues and suggest that any disease with chronic elevation of TGF-β would benefit by inhibiting smad2 and smad3 signaling pathways.

TGF-β is also implicated in peritoneal adhesions Saed G. M., Zhang W., Chegini N., Holmdahl L., and Diamond M. P., *Wound Repair Regeneration.* 7(6):504–510, 1999 November–December. Therefore, inhibitors of ALK5 would be beneficial in preventing peritoneal and sub-dermal fibrotic adhesions following surgical procedures.

TGFβ1-antibodies prevent transplanted renal tumor growth in nude mice through what is thought to be an anti-angiogenic mechanism Ananth S, et al, *Journal of The American Society of Nephrology Abstracts,* 9: 433A (Abstract). While the tumor itself is not responsive to TGF-β, the surrounding tissue is responsive and supports tumor growth by neovascularization of the TGFβ secreting tumor. Thus, antagonism of the TGF-β pathway should prevent metastasis growth and reduce cancer burden.

Surprisingly, it has now been discovered that a class of 2-pyridyl substituted triarylimidazoles of formula (I), function as potent and selective non-peptide inhibitors of ALK5 kinase and therefore, have utility in the treatment and prevention of various disease states mediated by ALK5 kinase mechanisms, such as chronic renal disease, acute renal disease, wound healing, arthritis, osteoporosis, kidney disease, congestive heart failure, ulcers, ocular disorders, corneal wounds, diabetic nephropathy, impaired neurological function, Alzheimer's disease, trophic conditions, atherosclerosis, peritoneal and sub-dermal adhesion, any disease wherein fibrosis is a major component, including, but not limited to lung fibrosis and liver fibrosis, and restenosis.

According to the invention there is provided a compound of formula (I) or a pharmaceutically acceptable salt thereof:

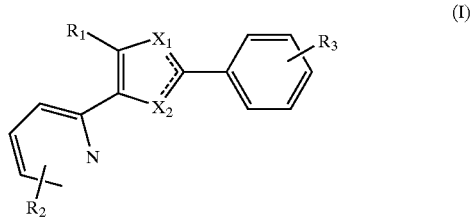

(I)

wherein $R_1$ is naphthyl or phenyl optionally substituted with one or more substituents selected from the group consisting of halo, —O—$C_{1-6}$alkyl, —S—$C_{1-6}$alkyl, $C_{1-6}$alkyl, $C_{1-6}$haloalkyl, —O—$(CH_2)_n$—Ph, —S—$(CH_2)_n$—Ph, cyano, phenyl, and $CO_2R$, wherein R is hydrogen or $C_{1-6}$alkyl, and n is 0, 1, 2 or 3; or $R_1$ is phenyl fused with an aromatic or non-aromatic cyclic ring of 5–7 members wherein said cyclic ring optionally contains up to three heteroatoms, independently selected from N, O and S;

$R_2$ is H, $C_{1-6}$alkyl, $C_{1-6}$alkoxy, phenyl, $NH(CH_2)_n$—Ph, NH—$C_{1-6}$alkyl, halo, or alkoxy;

$R_3$ is COOH, tetrazole, CN, $NO_2$, OH, —S—$C_{1-6}$alkyl, —SO—$C_{1-6}$alkyl, —O—$C_{1-6}$alkyl, $SONH_2$, CHO, $CH_2OH$, $(CH_2)_nNH_2$, $CONHOR'$, $O(CH_2)_nCO_2R'$, $O(CH_2)_n$ $CONHR'$, $CONHR'$, $(CH_2)_nCO_2R'$, or $(CH_2)_nCONHR'$ wherein R' is hydrogen or $C_{1-6}$alkyl, and n is 0, 1, 2 or 3; and one of $X_1$ and $X_2$ is N or CR", and the other is NR" or CHR" wherein R" is hydrogen, $C_{1-6}$alkyl, or $C_{3-7}$cycloalkyl; or when one of $X_1$ and $X_2$ is N or CR" then the other may be S or O;

provided that the compound is not one in which $R_1$ is naphthyl or phenyl optionally substituted with one or more substituents selected from the group consisting of halo, —O—$C_{1-6}$alkyl, —S—$C_{1-6}$alkyl, $C_{1-6}$alkyl, —O— $(CH_2)_n$—Ph, —S—$(CH_2)_n$—Ph, cyano, phenyl, and $CO_2R$, wherein R is hydrogen or $C_{1-6}$alkyl and n is 0, 1, 2 or 3; or $R_1$ is phenyl fused with an aromatic or non-aromatic cyclic ring of 5–7 members wherein said cyclic ring optionally contains up to two heteroatoms, independently selected from N, O and S;

and $R_2$ is H, $NH(CH_2)_n$—Ph or NH—$C_{1-6}$alkyl;

and $R_3$ is $CO_2H$, $CONH_2$, CN, $NO_2$, $C_{1-6}$alkylthio, $SO_2$—$C_{1-6}$alkyl, $C_{1-6}$alkoxy, $SONH_2$, CONHOH, $NH_2$, CHO, $CH_2OH$, $CH_2NH_2$, or $CO_2R$, wherein R is hydrogen or $C_{1-6}$alkyl.

As used herein, the double bond indicated by the dotted lines of formula (I), represents the possible tautomeric ring forms of the compounds falling within the scope of this invention. It will be understood that when either $X_1$ or $X_2$ are carbon, then the double bond could be either to the carbon or the heteroatom. When $X_1$ and $X_2$ are both carbon, then the double bond could be to either $X_1$ or $X_2$. When $X_1$ and $X_2$ are both heteroatoms, then the double bond is to the unsubstituted heteroatom.

Preferably $R_1$ is optionally substituted naphthyl or phenyl. More preferably $R_1$ is phenyl optionally substituted with one or more substituents selected from the group consisting of halo, $C_{1-6}$alkoxy, $C_{1-6}$alkylthio, and phenyl; or $R_1$ is phenyl fused with an aromatic or non-aromatic cyclic ring of 5–7 members wherein said cyclic ring optionally contains up to two heteroatoms, independently selected from N, O and S, and is optionally substituted by =O; for example $R_1$ represents benzo[1,3]dioxolyl, 2,3-dihydrobenzo[1,4]dioxinyl, benzoxazolyl, benzothiazolyl, quinoxalinyl, benzo[1,2,5]oxadiazolyl, benzo[1,2,5] thiadiazolyl, [1,2,4]triazolo[1,5-a]pyridyl, dihydrobenzofuranyl, benzo[1,4]oxazinyl-3-one or benzoxazolyl-2-one.

Preferably $R_2$ is other than hydrogen. When $R_2$ is other than hydrogen it is preferably positioned ortho to the nitrogen of the pyridyl ring. $R_2$ is preferably methyl.

Preferably $R_3$ is $CO_2H$, $CONH_2$, CONHOH, $CH_2OH$, CN or tetrazole.

Preferably one of $X_1$ and $X_2$ is N or CR", and the other is NR" or CHR' wherein R" is hydrogen, $C_{1-6}$alkyl, or $C_{3-7}$cycloalkyl, provided that at least one of $X_1$ and $X_2$ is N or NR"; or one of one of $X_1$ and $X_2$ is N and the other is O. More preferably one of $X_1$ and $X_2$ is N and the other is NR".

Preferably each R" is hydrogen.

The compounds for use in the methods of the invention preferably have a molecular weight of less than 800, more preferably less than 600.

Specific compounds of the invention which may be mentioned include the following:

4-(4-Benzo[1,3]dioxol-5-yl-5-pyridin-2-yl-1H-imidazol-2-yl)phenol;

4-(4-Benzo[1,3]dioxol-5-yl-5-pyridin-2-yl-1H-imidazol-2-yl)-N-methyl-benzamide;

4-(4-Benzo[1,3]dioxol-5-yl-5-pyridin-2-yl-1H-imidazol-2-yl)-N-methoxy-benzamide;

2-{4-Benzo[1,3]dioxol-5-yl-2-[4-(2H-tetrazol-5-yl)-phenyl]-1H-imidazol-5-yl}-pyridine;

[4-(4-Benzo[1,3]dioxol-5-yl-5-pyridin-2-yl-1H-imidazol-2-yl)-phenoxy]-acetic acid;

4-[4-(4-Fluoro-3-methoxyphenyl)-5-(6-methylpyridin-2-yl)-1H-imidazol-2-yl]-benzonitrile;

4-[4-(4-Fluoro-3-methoxyphenyl)-5-(6-methylpyridin-2-yl)-1H-imidazol-2-yl]-benzamide;

4-[4-(3-Fluoro-4-methoxyphenyl)-5-(6-methylpyridin-2-yl)-1H-imidazol-2-yl]benzonitrile;

4-[4-(3-Fluoro-4-methoxyphenyl)-5-(6-methylpyridin-2-yl)-1H-imidazol-2-yl]benizamide;

4-[4-Benzo[1,2,5]oxadiazol-5-yl-5-(6-methyl-pyridin-2-yl)-1H-imidazol-2-yl]benzonitrile;

4-[4-Benzo[1,2,5]oxadiazol-5-yl-5-(6-methylpyridin-2-yl)-1H-imidazol-2-yl]benzamide;

4-[4-(6-Methoxynaphthalen-2-yl)-5-(6-methylpyridin-2-yl)-1H-imidazol-2-yl]benzonitrile;

4-[4-(6-Methoxynaphthalen-2-yl)-5-(6-methylpyridin-2-yl)-1H-imidazol-2-yl]benzamide;

4-[4-Benzo[1,2,5]thiadiazol-5-yl-5-(6-methylpyridin-2-yl)-1H-imidazol-2-yl]benzonitrile;

4-[4-Benzo[1,2,5]thiadiazol-5-yl-5-(6-methylpyridin-2-yl)-1H-imidazol-2-yl]benzamide;

4-[4-Benzo[1,3]dioxol-5-yl-5-(6-methylpyridin-2-yl)-1H-imidazol-2-yl]benzonitrile;

4-[4-Benzo[1,3]dioxol-5-yl-5-(6-methylpyridin-2-yl)-1H-imidazol-2-yl]benzamide;

6-[2-(4-Cyanophenyl)-5-(6-methylpyridin-2-yl)-1H-imidazole-4-yl]-quinoxaline; and 6-[2-(4-Carboxamidophenyl)-5-(6-methylpyridin-2-yl)-1H-imidazole-4-yl]-quinoxaline;

and pharmaceutically acceptable salts thereof.

Suitable, pharmaceutically acceptable salts of the compounds of formula (I) include, but are not limited to, salts with inorganic acids such as hydrochloride, sulfate, phosphate, diphosphate, hydrobromide, and nitrate, or salts with an organic acid such as malate, maleate, fumarate, tartrate, succinate, citrate, acetate, lactate, methanesulfonate, p-toluenesulfonate, palmitate, salicylate, and stearate.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Certain of the compounds of formula (I) may exist in the form of optical isomers, e.g. diastereoisomers and mixtures of isomers in all ratios, e.g. racemic mixtures. The invention includes all such forms, in particular the pure isomeric forms. The different isomeric forms may be separated or resolved one from the other by conventional methods, or any given isomer may be obtained by conventional synthetic methods or by stereospecific or asymmetric syntheses.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (1) or pharmaceutically acceptable derivative thereof.

The term "$C_{1-6}$alkyl" as used herein whether on its own or as part of a larger group e.g. $C_{1-6}$alkoxy, means a straight or branched chain radical of 1 to 6 carbon atoms, unless the chain length is limited thereto, including, but not limited to methyl, ethyl, n-propyl, isopropyl, n-butyl, sec-butyl, isobutyl and tert-butyl.

$C_{1-6}$ haloalkyl groups may contain one or more halo atoms, a particular $C_{1-6}$ haloalkyl group that may be mentioned in $CF_3$.

The terms "halo" or "halogen" are used interchangeably herein to mean radicals derived from the elements chlorine, fluorine, iodine and bromine.

The term "cycloalkyl" is used herein at all occurrences to mean cyclic radicals, preferably of 3 to 7 carbons, including but not limited to cyclopropyl, cyclopentyl and cyclohexyl.

The term "aryl" is used herein at all occurrences to mean 5- to 14-membered substituted or unsubstituted aromatic ring(s) or ring systems which may include bi- or tri-cyclic systems, including, but not limited to phenyl, naphthyl.

The term "ALK5 inhibitor" is used herein at all occurrences to mean a compound, other than inhibitory smads, e.g. smad6 and smad7, which selectively inhibits the ALK5 receptor preferentially over p38 or type II receptors.

The term "ALK5 mediated disease state" is used herein at all occurrences to mean any disease state which is mediated (or modulated) by ALK5, for example a disease which is modulated by the inhibition of the phosphorylation of smad 2/3 in the TGF-1β signaling pathway.

The term "ulcers" is used herein at all occurrences to include, but not to be limited to, diabetic ulcers, chronic ulcers, gastric ulcers, and duodenal ulcers.

The compounds of formula (I) can be prepared by art-recognized procedures from known or commercially available starting materials. If the starting materials are unavailable from a commercial source, their synthesis is described herein, or they can be prepared by procedures known in the art.

Specifically, compounds of formula (I) wherein one of $X_1$ and $X_2$ is N and the other is NH may be prepared as illustrated in Scheme 1 for compounds wherein $X_1$ is N and $X_2$ is NH. Using the method detailed in U.S. Pat. No. 3,940,486, N-methoxy-N-methylaryl amide is alkylated with the anion generated from a 2(6)-methylpyridine to give a ketone. The ketone is treated with sodium nitrite to form the oxime which is condensed with an aldehyde and NH$_4$OAc to give a hydroxy imidazole. The hydroxy imidazole may then be reduced with triphenylphosphite by the method described in U.S. Pat. No. 5,656,644 to give the corresponding imidazole. The hydroxy imidazoles used as intermediates in this reaction are also novel and as such form part of the present invention.

Scheme 1

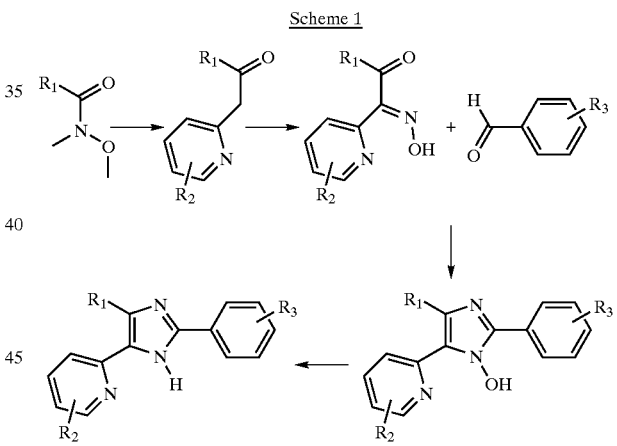

Alternatively, the ketone may be oxidised to a diketone with HBr in DMSO. This diketone can then be condensed with a suitably substituted benzaldeyde and ammonium acetate to give the imidazole according to the method outlined in WO 98/56788 and as illustrated in Scheme 2 for compounds wherein $X_1$ is N and $X_2$ is NH.

Scheme 2

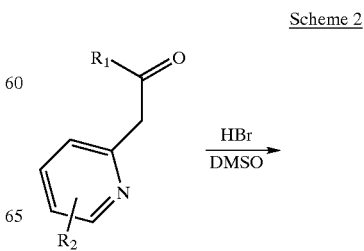

-continued

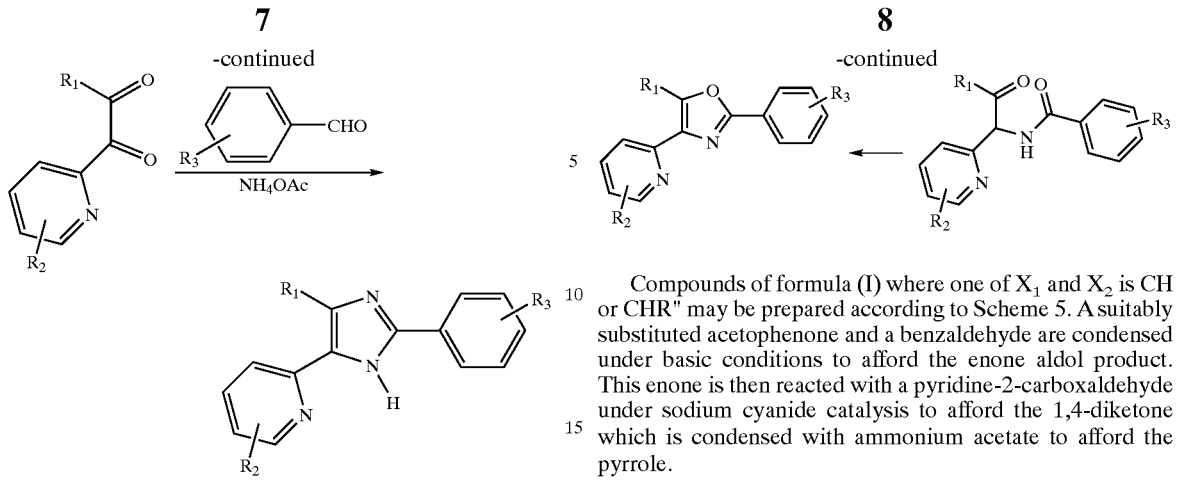

Non-selective alkylation of the imidazole nitrogen (using one of the procedures outlined in N. J. Liverton et al; *J. Med. Chem.*, 1999, 42, 2180–2190) with a compound of formula L-R" wherein L is a leaving group, e.g. halo, sulfonate or triflate, will yield both isomers of the compounds where one of $X_1$ or $X_2$ is NR" wherein R" is $C_{1-6}$alkyl, or $C_{3-7}$cycloalkyl, as illustrated in Scheme 3, the isomers can be separated by chromatographic methods.

Scheme 3

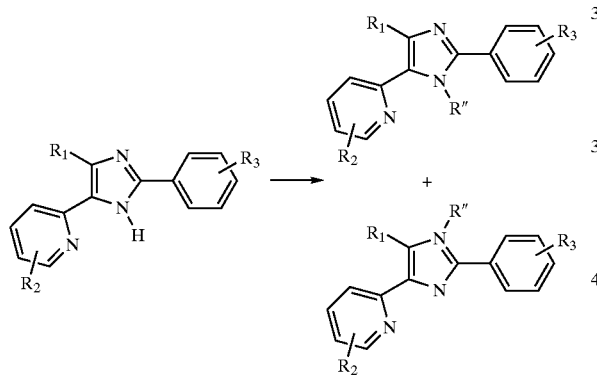

Compounds of formula (I) wherein one of $X_1$ and $X_2$ is N and the other is O may be prepared according to Scheme 4. The oximino ketone may be reduced via catalytic hydrogen to afford the amino ketone which can be further reacted with an appropriately substituted benzoyl chloride compound. Reaction of the amide product with thionyl chloride affords the oxazole product.

Scheme 4

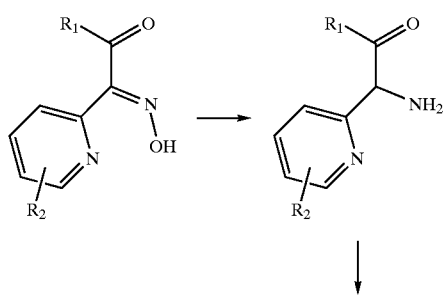

-continued

Compounds of formula (I) where one of $X_1$ and $X_2$ is CH or CHR" may be prepared according to Scheme 5. A suitably substituted acetophenone and a benzaldehyde are condensed under basic conditions to afford the enone aldol product. This enone is then reacted with a pyridine-2-carboxaldehyde under sodium cyanide catalysis to afford the 1,4-diketone which is condensed with ammonium acetate to afford the pyrrole.

Scheme 5

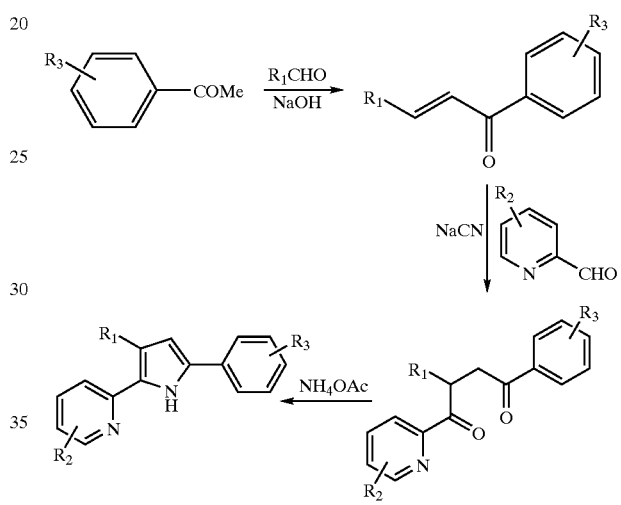

During the synthesis of the compounds of formula (I) labile functional groups in the intermediate compounds, e.g. hydroxy, carboxy and amino groups, may be protected. A comprehensive discussion of the ways in which various labile functional groups may be protected and methods for cleaving the resulting protected derivatives is given in for example *Protective Groups in Organic Chemistry*, T. W. Greene and P. G. M. Wuts, (Wiley-Interscience, New York, 2nd edition, 1991).

Further details for the preparation of compounds of formula (I) are found in the examples.

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I) or pharmaceutically acceptable salts thereof.

According to a further aspect of the present invention there is provided the use of a compound of formula (I) or a pharmaceutically acceptable salt thereof, in the manufacture of a medicament for the treatment of a disease mediated by the ALK5 receptor in mammals.

ALK5-mediated disease states, include, but are not limited to, chronic renal disease, acute renal disease, wound healing, arthritis, osteoporosis, kidney disease, congestive heart failure, ulcers, ocular disorders, corneal wounds, diabetic nephropathy, impaired neurological function, Alzheimer's disease, trophic conditions, atherosclerosis, any disease wherein fibrosis is a major component, including, but not limited to peritoneal and sub-dermal adhesion, lung fibrosis and liver fibrosis, and restenosis.

By the term "treating" is meant either prophylactic or therapeutic therapy.

According to a further aspect of the present invention there is provided a method of inhibiting the TGF-β signaling pathway in mammals, for example, inhibiting the phosphorylation of smad2 or smad3 by the type I or activin-like kinase ALK5 receptor.

According to a further aspect of the present invention there is provided a method of inhibiting matrix formation in mammals by inhibiting the TGF-β signaling pathway, for example, inhibiting the phosphorylation of smad2 or smad3 by the type I or activin-like kinase ALK5 receptor.

The pharmaceutically effective compounds of formula (I) and pharmaceutically acceptable salts thereof, may be administered in conventional dosage forms prepared by combining a compound of formula (I) ("active ingredient") with standard pharmaceutical carriers or diluents according to conventional procedures well known in the art. These procedures may involve mixing, granulating and compressing or dissolving the ingredients as appropriate to the desired preparation.

According to a further aspect of the present invention there is provided a pharmaceutical composition comprising a compound of formula (I), or a pharmaceutically acceptable salt thereof, and a pharmaceutically acceptable carrier or diluent.

The pharmaceutical compositions of the invention may be formulated for administration by any route, and include those in a form adapted for oral, topical or parenteral administration to mammals including humans.

The compositions may be formulated for administration by any route. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminum stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

It will be recognized by one of skill in the art that the optimal quantity and spacing of individual dosages of a formula (I) compound will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of the formula (I) compound given per day for a defined number of days, can be ascertained by those skilled in the art using conventional course of treatment determination tests.

No toxicological effects are indicated when a compound of formula (I) or a pharmaceutically acceptable derivative thereof is administered in the above-mentioned dosage range.

All publications, including, but not limited to, patents and patent applications cited in this specification, are herein incorporated by reference as if each individual publication were specifically and individually indicated to be incorporated by reference herein as though fully set forth.

The following examples are to be construed as merely illustrative and not a limitation on the scope of the invention in any way. In the Examples, mass spectra were performed using an Hitachi Perkin-Elmer RMU-6E with chemical ionization technique (CI) or a Micromass Platform II instrument with electrospray (ES) ionization technique.

EXAMPLES

Example 1

4-(4-Benzo[1,3]dioxol-5-yl-5-pyridin-2-yl-1H-imidazol-2-yl)phenol

The title compound was prepared from 4-benzo[1,3]dioxol-5-yl-2-(4-hydroxyphenyl-5-pyridin-2-ylimidazol-1-ol using the procedure in U.S. Pat. No. 5,656,644 (Example 1) to prepare 2-(4-cyanophenyl)-4-(4-fluorophenyl)-5-(4-pyridyl)-1H-imidazole. $^1$H NMR (250 MHz; CD$_3$OD) δ: 5.92 (2H, s), 6.83–6.98 (5H, m), 7.35–7.45 (2H, m), 7.74–7.82 (3H, m), 8.59 (1H, d): m/z [ESMS]: 358.1 [M+H]$^\oplus$.

Example 2

4-(4-Benzo[1,3]dioxol-5-yl-5-pyridin-2-yl-1H-imidazol-2-yl)-N-methyl-benzamide 4-(4-Benzo[1,3]dioxol-5-yl-5-pyridin-2-yl-1H-imidazol-2-yl)benzoyl chloride hydrochloride (100 mg; 0.23 mmol) was suspended in tetrahydrofuran (5 ml) and treated with a solution of methylamine in water (40% w/v; ml) and the resulting mixture stirred at ambient temperature for 18 h. The title compound (55 mg; 60%) was obtained as a brown powder by filtration, washing with water and drying at 40° C. under reduced pressure. $^1$H NMR (250 MHz; CD$_3$OD) δ: 2.84 (3H, s), 5.89 (2H, s), 6.76 (1H, d), 6.85–7.80 (5H, m), 7.82 (2H, d), 8.00 (2H, d), 8,49 (1H, br); m/z (ESMS): 399 [M+HM]$^\oplus$.

Example 3

4-(4-Benzo[1,3]dioxol-5-yl-5-pyridin-2-yl-1H-imidazol-2-yl)-N-methoxy-benzamide 4-(4-Benzo[1,3]dioxol-5-yl-5-pyridin-2-yl-1H-imidazol-2-yl)benzoyl chloride hydrochloride (100 mg; 0.23 mmol) was suspended in dichloromethane (10 ml), N,O-dimethyl hydroxylamine hydrochloride (38 mg; 0.45 mmol) added followed by triethylamine (0.16 ml; 1.1 mmol). The resulting mixture was stirred at ambient temperature for 18 h. The mixture was evaporated to dryness under reduced pressure and the residue partitioned between ethyl acetate and water. The organic phase was washed with water, saturated brine, dried (MgSO$_4$) and evaporated to dryness under reduced pressure. The title compound (4 mg; 4%) was obtained by high performance liquid chromatography. $^1$H NMR (250 MHz; CD$_3$OD) δ: 3.74 (3H, s), 6.00 (2H, s), 6.94 (1H, d,), 7.04–7.08 (2H, m), 7.50–7.70 (2H, m), 7.85 (2H, d), 8.00–8.20 (3H, m), 8.59 (1H, d); m/z (ESMS): 415.1 [M+H]$^\oplus$.

Example 4

2-{4-Benzo[1,3]dioxol-5-yl-2-[4-(2H-tetrazol-5-yl)-phenyl]-1H-imidazol-5-yl}-pyridine Prepared according to the method of Example 1 from 2-[4-benzo[1,3]dioxol-5-yl-5-pyridin-2-yl-2-[4-(1H-tetrazol-5-yl)-phenyl]imidazol-1-ol (19%). $^1$H NMR (250 MHz; CD$_3$OD) δ: 6.03 (2H, s), 6.96–7.12 (3H, m), 7.59–7.74 (2H, m), 8.10–8.25 (5H, m), 8.61–8.63 (1H, m); m/z [ESMS]: 382.0 [M+H−N$_2$]$^\oplus$.

Example 5

4-(4-Benzo[1,3]dioxol-5-yl-5-pyridin-2-yl-1H-imidazol-2-yl)-phenoxy]-acetic acid 4-(4-Benzo[1,3]dioxol-5-yl-5-pyridin-2-yl-1H-imidazol-2-yl)-phenol (357 mg; 1 mmol) was dissolved in tetrahydrofuran (20 ml) under argon and treated portionwise with sodium hydride (60% dispersion in oil; 60 mg; 1.5 mmol). When effervescence had ceased, bromoacetonitrile (178.5 mg; 103.5 µl ; 1.5 mmol) was added and the mixture was stirred at ambient temperature for 18 h. Saturated aqueous ammonium chloride solution was added and the nitrile extracted into ethyl acetate. The organic extracts were combined, washed with water, saturated brine, dried (MgSO$_4$) and evaporated to dryness under reduced pressure. The residue was purified by chromatography through SiO$_2$, eluting with ethyl acetate in 60–80° petroleum ether (50→100% ethyl acetate gradient), to give [4-(4-benzo[1,3]dioxol-5-yl-5-pyridin-2-yl-1H-imidazol-2-yl)-phenoxy]-acetonitrile (120 mg; 30%). This nitrile (120 mg; 0.31 mmol) was treated with ethanol (30 ml) and 2M aq. sodium hydroxide solution and the resulting mixture heated at reflux for 3 h. Cooled and evaporated to dryness under reduced pressure. The residue was treated with water and acidified to pH4–5 with 5M hydrochloric acid. The yellow precipitate was collected by filtration, washed with water and dried at 40° C. under reduced pressure (92 mg; 73%). $^1$H NMR (250 MHz; CD$_3$OD) δ: 4.77 (2H, s), 6.12 (2H, s), 7.02 (1H, d), 7.12–7.14 (2H, m), 7.18 (2H, d), 7.44–7.49 (1H, m), 7.60 (1H, d), 7.86–7.92 (1H, m), 8.05 (2H, d), 8.72 (1H, d); m/z (API): 416.3 [M+H]$^\oplus$.

Example 6

4-[4-(4-Fluoro-3-methoxyphenyl)-5-(6-methylpyridin-2-yl)-1H-imidazol-2-y]-benzonitrile Prepared according to the method of Example 1 from 4-[4-(fluoro-3-methoxyphenyl)-1-hydroxy-5-(6-methylpyridin-2-yl)-1H-imidazol-2-yl]-benzonitrile. $^1$H NMR (CDCl$_3$) δ: 2.51 (3H, s), 3.91 (3H, s), 7.02–7.16 (3H, m), 7.33 (2H, d), 7.50 (1H, t), 7.69 (2H, d), 8.06 (2H, d, 8 Hz); m/z (API) 385 (M+H$^+$).

Example 7

4-[4-(4-Fluoro-3-methoxyphenyl)-5-(6-methylpyridin-2-yl)-1H-imidazol2-yl]-benzamide 4-[4-(Fluoro-3-methoxyphenyl)-5-(6-methylpyridin-2-yl)-1H-imidazol-2-yl]-benzonitrile (1 g, 2.6 mmol) (prepared according to the method of Example 1) and potassium hydroxide (0.53 g) were added to tert-butanol (50 ml) and heated overnight at reflux. On cooling, the solid mixture was diluted with ethyl acetate and evaporate in vacuo. The residue was then partitioned between dichloromethane and water. The organic phase was dried over sodium sulfate and concentrated in vacuo to afford the title compound. $^1$H NMR(CDCl$_3$) δ: 2.57 (3H, s), 3.91 (3H, s), 7.01 (1H, d), 7.09–7.21 (2H, m), 7.33 (2H, d), 7.46 (1H, t), 7.90 (2H, d), 8.06 (2H, d); m/z (API) 403 (M+H$^+$).

Example 8

4-[4-(3-Fluoro-4-methoxyphenyl)-5-(6-methylpyridin-2-yl)-1H-imidazol-2-yl]benzonitrile Prepared according to the method of Example 1 from 4-[4-(3-Fluoro-4-methoxyphenyl)-1-hydroxy-5-(6- methylpyridin-2-yl)-1H-imidazol-2-yl]benzonitrile. $^1$H NMR (CDCl$_3$) δ: (2.48 (3H, s), 3.96 (3H, s), 7.00–7.08 (2H, m), 7.30–7.57 (4H, m), 7.67 (2H, d), 8.03 (2H, d); m/z(API) 405 (M+H$^+$, 100%).

Example 9

4-[4-(3-Fluoro-4-methoxy-phenyl)-5-(6methyl-pyridin-2-yl)-1H-imidazol-2-yl]benzamide Prepared according to the method of Example 7 from 4-[4-(3-fluoro-4-methoxy-phenyl)-5-(6-methyl-pyridin-2-yl)-1H-imidazol-2-yl]benzonitrile. $^1$H NMR (CDCl$_3$) δ: 2.57 (3H, s), 3.96 (3H, s), 7.00–7.09 (2H, m), 7.32 (1H, d), 7.39–7.50 (3H, m), 7.89 (2H, d); m/z(API) 403 (M+H$^+$, 100%).

Example 10

4-[4-Benzo[1,2,5]oxadiazol-5-yl-5-(6-methyl-pyridin-2-yl)-1H-imidazol-2-yl]benzonitrile Prepared according to the method of Example 1 from 4-[4-benzo[1,2,5]oxadiazol-5-yl-1-hydroxy-5-(6-methyl-pyridin-2-yl)-1H-imidazol-2-yl]benzonitrile. $^1$H NMR (CDCl$_3$) δ: 2.66 (3H, s), 6.85–6.97 (1H, m), 7.39 (1H, d), 7.52–7.76 (1H, m), 7.75 (3H, t), 7.87 (1H, d), 7.92–7.98 (1H, m), 8.12 (2H, d); m/z(API) 379 (M+H$^+$, 100%).

Example 11

4-[4-Benzo[1,2,5]oxadiazol-5-yl-5-(6-methyl-pyridin-2-yl)-1H-imidazol-2-yl]benzamide Prepared according to the method of Example 7 from 4-[4-benzo[1,2,5]oxadiazol-5-yl-5-(6-methyl-pyridin-2-yl)-1H-imidazol-2-yl]benzonitrile; m/z (API) 397.

Example 12

4-[4-(6-Methoxynaphthalen-2-yl)-5-(6-methylpyridin-2-yl)-1H-imidazol-2-yl]benzonitrile Prepared according to the method of Example 1 from 4 [4-(6-methoxynaphthalen-2-yl)-1-hydroxy-5-(6-methylpyridin-2-yl)-1H-imidazol-2-yl]benzonitrile. $^1$H NMR (CDCl$_3$) δ: 2.79 (3H, s), 3.92 (3H, s), 7.27 (1H, d), 7.45 (1H, s), 7.45 (1H, s), 7.54 (1H, d), 7.68 (2H, d), 7.88–7.98 (2H, m), 8.07 (2H, d), 8.17 (2H, t), 8.25 (1H, s), 8.45 (2H, d); m/z(API) 417 (M+H$^+$, 100%).

Example 13

4-[4-(6-Methoxynaphthalen-2-yl)-5-(6-methylpyridin-2-yl)-1H-imidazol-2-yl]benzamide Prepared according to the method of Example 7 from 4-[4-(6-methoxynaphthalen-2-yl)-5-(6-methylpyridin-2-yl)-1H-imidazol-2-yl]benzonitrile. $^1$H NMR (CDCl$_3$) δ: 2.75 (1H, s), 3.92 (1H, s), 7.27 (1H, d), 7.43–7.71 (4H, m), 7.88–7.97 (2H, m), 8.10 (2H, d), 8.17–8.24 (2H,m), 8.26 (1H,s), 8.36 (2H, d); m/z(API) 435 (M+H$^+$, 100%).

Example 14

4-[4-Benzo[1,2,5]thiadizol-5-yl-5-(6-methylpyridin-2-yl)-1H-imidazol-2-yl]benzonitrile 1-Benzo[1,2,5]thiadiazol-5-yl-2-(6-methyl-pyridin-2-yl)-ethane-1,2-dione (5.2 g, 18.4 mmol) was dissolved in tert-butyl methyl ether (100 ml) and treated with 4-cyanobenzaldehyde (2.4 g). Ammonium acetate (14.2 g) in methanol (20 ml) was added and the reaction was heated at reflux temperature for 3 hours. The reaction mixture was partitioned between dichloromethane and water then, dichloromethane and brine. The dichloromethane layer was separated, dried (MgSO$_4$) and evaporated to dryness under reduce pressure. The title compound was isolated by silica gel column chromatography using a 1:1 ethyl acetate:petroleum spirit solution as eluent (400 mg, 5.5%). $^1$H NMR (CDCl$_3$) δ: 2.60 (3H, s), 7.08 (2H, d), 7.47–7.53 (2H,m), 7.77 (2 H, d), 7.95–8.17 (4H, m), 8.38 (1H, s); m/z(API) 395 (M+H$^+$, 100%).

Example 15

4-[4-Benzo[1,2,5]thiadiazol-5-yl-5-(6-methylpyridin-2-yl)-1H-imidazol-2-yl]benzamide Prepared according to the method of Example 7 from 4-[4-benzo [1,2,5]thiadiazol-5-yl-5-(6-methylpyridin-2-yl)-1H-imidazol-2-yl]benzonitrile. $^1$H NMR (CDCl$_3$) δ: 2.44 (3H, s), 6.94 (2H, d), 7.12 (1H, s), 7.58 (1H, t), 7.81 (2H, d), 8.13 (1H, d), 8.32 (1H, s), 8.57–8.64 (1H, m), 8.95 (1H, s); m/z(API) 413 (M+H$^+$, 100%).

Example 16

4-[4-Benzo[1,3]dioxol-5-yl-5-(6-methylpyridin-2-yl-1H-imidazol-2-yl]benzonitrile Prepared according to the method of Example 1 from 4-[4-benzo[1,3]dioxol-5-yl-1-hydroxy-5-(6-methylpyridin-2-yl-1H-imidazol-2-yl]benzonitrile. $^1$H NMR (CDCl$_3$) δ: 2.48 (3H, s), 6.03 (2H, d), 6.88 (1H, d), 7.00 (2H, d), 7.14 (1H, s), 7.17 (1H, d), 7.37 (1H, d), 7.49 (1H, t), 7.68 (2H, d), 8.02 (2H, d); m/z (API) 381 (M+H$^+$).

Example 17

4-[4-Benzo[1,3]dioxol-5-yl-5-(6-methylpyridin-2-yl)-1H-imidazol-2-yl]benzamide

Prepared according to the method of Example 7 from 4-[4-benzo[1,3]dioxol-5-yl-5-(6-methylpyridin-2-yl-1H-imidazol-2-yl]benzonitrile. $^1$H NMR (CDCl$_3$) δ: 2.48 (3H, s), 5.66 (1H, br. s), 6.01 (2H, d), 6.01 (1H, brs), 6.86 (1H, d), 6.98 (2H, d), 7.14 (2H, m), 7.33 (1H, d), 7.46 (1H, t), 7.77 (2H, d), 7.94 (2H, d); m/z (API) 399 (M+H$^+$).

Example 18

6-[2-(4-Cyanophenyl)-5-(6-methylpyridin-2-yl)-1H-imidazole-4-yl]-quinoxaline

A stirred solution of 6-(2-[6-methylpyridin-2-yl]-2-oxo-acetyl)quinoxaline (1.2 g, 4.3 mmole) in $^t$BuOMe/MeOH (90/10 ml) was treated with ammonium acetate (13 g, 169 mmole) and heated under reflux for 15 h. The volatile components were removed in vacuo and the residue subjected to flash chromatography (EtOAc/petrol 4:1) to give the title compound as a yellow solid (260 mg, 15%). $^1$H NMR (250 MHz; CDCl$_3$) δ: 8.89 (2H, br. s), 8.45 (1H, s), 8.19 (2H, s), 8.09 (2H, d), 7.75 (2H, d), 7.52 (1H, t), 7.39 (1H, d), 7.09 (1H, d), 2.49 (3H, s); m/z [ESMS]: 389 [M+H]$^+$.

Example 19

6-[2-(4-Carboxamidophenyl)-5-(6-methylpyridin-2-yl)-1H-imidazole-4-yl]-quinoxaline A stirred solution of 6-[2-(4-cyanophenyl)-5-[6-methylpyridin-2-yl]-2-oxo-acetyl)quinoxaline (200 mg, 0.52 mmole) in DMSO (10 ml) was treated with $H_2O_2$ (30% aq., 1 ml). After 15 h the solution was brought to pH5 with 2N HCl and loaded on to a solid phase cation exchange column. After washing with MeOH, the title compound was eluted with 0.2N $NH_3$ in MeOH, giving a yellow solid (32 mg, 15%). $^1$H NMR (250 MHz; $CD_3OD$) δ: 8.78 (2H, br. s), 8.24 (1H, s), 8.09 (2H, d), 7.98 (2H, s), 7.91 (2H, d), 7.61 (1H, t), 7.35 (1H, br. d), 7.16 (1H, d), 2.43 (3H, s); m/z [ESMS]: 407 [M+H]$^+$.

Intermediates

Preparation 1

4-(4-Benzo[1,3]dioxol-5-yl-5-pyridin-2-yl-1H-imidazol-2-yl)benzoyl chloride 4-(4-Benzo[1,3]dioxol-5-yl-5-pyridin-2-yl-1H-imidazol-2-yl)benzoic acid (prepared according to the method of Example 1) (379 mg; 0.98 mmol) was suspended in dry dichloromethane (20 ml) and treated with oxalyl chloride (2 ml) and N,N-dimethylformamide (1 drop). This mixture was stirred at ambient temperature for 5 h then evaporated to dryness under reduced pressure to give the title compound as a yellow powder.

Preparation 2

1-Benzo[1,2,5]thiadiazol-5-yl-2-(6-methyl-pyridin-2-yl)-ethane1,2-dione

1-Benzo[1,2,5]thiadiazol-5-yl -2-(6-methyl-pyridin-2-yl)-ethanone (5.88 g, 21.8 mmol) was dissolved in dimethyl sulfoxide (50 ml) heated to 60° C. Hydrogen bromide (7.1 ml of a 48% solution in water) was added dropwise and the reaction stirred for 3 hours at 60° C. The cooled reaction was poured into water (100 ml) and the pH adjusted to pH 8 with saturated sodium bicarbonate solution. The organic product was extracted into ethyl acetate (3×100 ml), dried over anhydrous magnesium sulfate and evaporated to dryness under reduced pressure (5.19 g, 84%); $^1$H NMR (250 MHz, $CDCl_3$) δ: 2.47 (3H, s), 7.40 (1H, d), 7.85 (1H, t), 8.06 (1H, d), 8.15 (1H, d), 8.28 (1H, d), 8.45 (1H, s); m/z(API) 284 (M+H$^+$, 100%).

Preparation 3

Quinoxaline-6-carbonyl chloride

A suspension of quinoxaline-6-carboxylic acid (1.8 g, 10.3 mmole) (*Chem. Ber.* 1953, 86, 1295) in $SOCl_2$ (30 ml) was stirred at 80° C. for 3 h. The resulting yellow solution was concentrated by distillation, and the residue treated with toluene and concentrated to dryness in vacuo giving a pale beige solid (2.0 g, quant.). m/z [ESMS]: 203 [M+EtOH−Cl]$^+$.

Preparation 4

6-[2-(6-Methylpyridin-2-yl)-acetyl]quinoxaline

A stirred solution of 2,6-lutidine (1.4 g, 13 mmole) in dry THF (100 ml) at −60° C. under Ar was treated dropwise with a solution of BuLi in hexane (2.5 M, 5.2 ml, 13 mmole). After 30 mins a solution of $Et_2AlCl$ in hexane (14 ml, 14 mmole) was added dropwise and the solution warmed to 20° C. After a further 30 mins the solution was cooled to −50° C. and transferred via canula to a stirred solution of quinoxaline-6-carbonyl chloride (2.0 g, 10.3 mmole) in THF (100 ml) at −60° C. Stirring was continued for 20 min and the solution quenched with sat. aq. $NH_4Cl$ solution and warmed to 20° C. The mixture was filtered through Kieselguhr and the filtrate worked up as normal (EtOAc, water, $Na_2SO_4$). Filtration through silica eluting with EtOAc gave the product as a yellow solid (1.65 g, 51%). m/z [ESMS]: 264 [M+H]$^+$.

Preparation 5

6-[2-(6-Methylpyridin-2-yl)-2-oxo-acetyl] quinoxaline

A stirred suspension of 6-(2-[6-methylpyridin-2-yl]-acetyl)quinoxaline (1.65 g, 6.3 mmole) in dry DMSO (50 ml) was heated to 70–80° C. (forming a yellow solution) and treated dropwise with aq. HBr (48%, 6 ml). After 2 h the solution was cooled, poured over ice-water and brought to pH 10 with $K_2CO_3$. Extraction with EtOAc (3×), drying over $Na_2SO_4$, filtration and concentration to dryness in vacuo gave the title compound as a crimson oil (1.5 g, 86%). m/z [ESMS]: 278 [M+H]$^+$.

Biological Data

The biological activity of the compounds of the invention may be assessed using the following assays:

Method for Evaluating ALK5 Kinase Phosphorylation of Smad3

Basic Flash-Plates (NEN Life Sciences) were coated by pipetting 100 micro liter of 0.1 molar sodium bicarbonate (pH 7.6), containing 150 nanograms of the fusion protein glutathion-S-transferase-smad3/100 micro liter of coating buffer. Plates were covered and incubated at room temperature for 10–24 hours. Then the plates were washed 2 times with 200 micro liter of coating buffer (0.1 molar sodium bicarbonate) and allowed to air dry for 2–4 hours.

For the phosphorylation reaction each well received 90 microliter containing 50 millimolar HEPES buffer (pH 7.4); 5 millimolar $MgCl_2$; 1 millimolar $CaCl_2$; 1 millimolar ditlhiothreitol; 100 micromolar guanosine triphosphate; 0.5 micro Ci/well gamma$^{33}$P-adenosine triphosphate (NEN Life Sciences) and 400 nanograms of a fusion protein of glutathion-S-transferase at the N-terminal end of the kinase domain of ALK5 (GST-ALK5). Background counts were measured by not adding any GST-ALK5. Inhibitors of ALK5 were evaluated by determining the activity of the enzyme in the presence of various compounds. Plates were incubated for 3 hours at 30° C. After incubation the assay buffer was removed by aspiration and the wells were washed 3 times with 200 microliter cold 10 millimolar sodium pyrophosphate in phosphate buffered saline. The last wash was aspirated and blotted plate dry. Plate was then counted on a Packard TopCount.

Fluorescence Anisotropy Kinase Binding Assay

The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10×$K_i$) of a potent inhibitor the anisotropy of the unbound fluorescent ligand is measurably different from the bound value.

The concentration of kinase enzyme should preferably be 1×$K_f$. The concentration of fluorescent ligand required will depend on the instrumentation used, and the fluorescent and physicochemical properties. The concentration used must be lower than the concentration of kinase enzyme, and preferably less than half the kinase enzyme concentration. A typical protocol is:

All components dissolved in Buffer of final composition 50 mM HEPES, pH 7.5, 1 mM CHAPS, 1 mM DTT, 10 mM $MgCl_2$ 2.5% DMSO.

ALK5 Enzyme concentration: 4 nM
Fluorescent ligand concentration: 1 nM
Test compound concentration: 0.1 nM–100 uM
Components incubated in 10 ul final volume in LJL HE 384 type B black microtitre plate until equilibrium reached (5–30 mins)
Fluorescence anisotropy read in LJL Acquest.
Definitions
$K_i$=dissociation constant for inhibitor binding
$K_f$=dissociation constant for fluorescent ligand binding
The fluorescent ligand is the following compound:

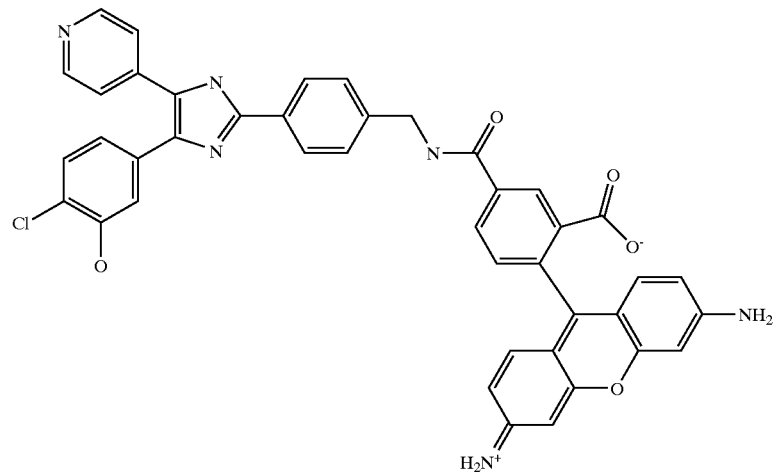

which is derived from 5-[2-(4-aminomethylphenyl)-5-pyridin-4-yl-1H-imidazol-4-yl]-2-chlorophenol and rhodamine green.

Inhibition of Matrix Markers: Northern Blot Protocol

Data confirming activity in the enzyme assay was obtained as follows.

A498 renal epithelial carcinoma cell lines were obtained from ATCC and grown in EMEM medium supplemented with 10% fetal calf serum, penicillin (5 units/ml) and streptomycin (5 ng/ml). A498 cells were grown to near confluence in 100 mm dishes, serum-starved for 24 hours, pre-treated with compounds for 4 hours followed by a 10 ng/ml addition of TGF-beta1 (R&D Systems, Inc., Minneapolis Minn.). Cells were exposed to TGF-beta1 for 24 hours. Cellular RNA was extracted by acid phenol/chloroform extraction (Chomczynski and Sacchi, 1987). Ten micrograms of total RNA were resolved by agarose gel electrophoresis and transferred to nylon membrane (GeneScreen, NEN Life Sciences, Boston Mass.). Membranes were probed with 32P-labeled cDNA probes (Stratagene, La Jolla, Calif.) for fibronectin mRNA. Membranes were exposed to phosphorimaging plates and bands were visualized and quantified with ImageQuant software (Molecular Dynamics, Sunnyvale, Calif.).

Inhibition of Matrix Markers: Western Blot Protocol

Data confirming activity in the enzyme assay was obtained as follows.

Cells were grown to near confluence in flasks, starved overnight and treated with TGF-beta and compounds. Cells were washed at 24 or 48 hours after treatment with ice cold phosphate buffered saline, then 500 microliter of 2×loading buffer was added to plate and cells were scraped and collected in microcentrifuge tube. (2×loading buffer: 100 mM Tris-Cl, pH6.8, 4% sodium dodecyl sulfate, 0.2% bromophenol blue, 20% glycerol, 5% beta-mercaptoethanol). Cells were lysed in tube and vortexed. Sample was boiled for 10 minutes. 20 microliters of sample was loaded on 7.5% polyacrylamide gel (BioRad) and electrophoresed.

Size fractionated proteins in gel were transferred to nitrocellulose membrane by semidry blotting. Membrane was blocked overnight with 5% powdered milk in phosphate buffer saline (PBS) and 0.05% Tween-20 at 4 degrees C. After 3 washes with PBS/Tween membranes were incubated with primary antibody for 4 hours at room temperature. After three washes with PBS/Tween membrane was incubated with secondary antibody for 1 hour at room temperature. Finally, a signal was visualized with ECL detection kit from Amersham.

The compounds of this invention generally show ALK5 receptor modulator activity having $IC_{50}$ values in the range of 0.0001 to 10 μM.

What is claimed is:

1. A compound of formula (I) or a pharmaceutically acceptable salt thereof:

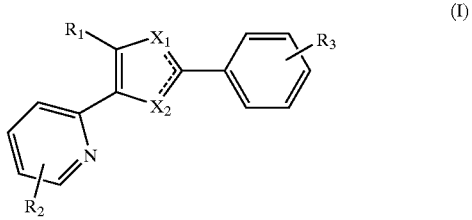

wherein $R_1$ is naphthyl, or phenyl optionally substituted with one or more substituents selected from the group consisting of halo, —O—$C_{1-6}$alkyl, —S—$C_{1-6}$alkyl, $C_{1-6}$alkyl, $C_{1-6}$haloalkyl, —O—$(CH_2)_n$-Ph, —S—$(CH_2)_n$-Ph, cyano, phenyl, and $CO_2R$, wherein R is hydrogen or $C_{1-6}$alkyl, and n is 0, 1, 2 or 3; or $R_1$ is phenyl fused with an aromatic or non-aromatic cyclic ring of 5–7 members wherein said cyclic ring optionally contains up to three heteroatoms, independently selected from N, O and S;

$R_2$ is H, $C_{1-6}$alkyl, $C_{1-6}$alkoxy, phenyl, $NH(CH_2)_n$-Ph, NH—$C_{1-6}$alkyl, halo or alkoxy;

$R_3$ is COOH, tetrazole, CN, $NO_2$, OH, —S—$C_{1-6}$alkyl, —SO—$C_{1-6}$alkyl, —O—$C_{1-6}$alkyl, $SONH_2$, CHO, $CH_2OH$, $(CH_2)_nNH_2$, CONHOR', $O(CH_2)_nCO_2R'$, O(CH$_2$)$_n$CONHR', CONHR', (CH$_2$)$_n$CO$_2$R', or (CH$_2$)$_n$CONHR' wherein R' is hydrogen or C$_{1-6}$alkyl, and n is 0, 1, 2 or 3; and one of X$_1$ and X$_2$ is N or CR", and the other is NR" or CHR" wherein R" is hydrogen, C$_{1-6}$alkyl, or C$_{3-7}$cycloalkyl; or when one of X$_1$ and X$_2$ is N or CR" then the other may be S or O;

provided that the compound is not one in which R$_1$ is naphthyl, or phenyl optionally substituted with one or more substituents selected from the group consisting of halo, —O—C$_{1-6}$alkyl, —S—C$_{1-6}$alkyl, C$_{1-6}$alkyl, —O—(CH$_2$)$_n$-Ph, —S—(CH$_2$)$_n$-Ph, cyano, phenyl, and CO$_2$R, wherein R is hydrogen or C$_{1-6}$alkyl and n is 0, 1, 2 or 3; or R$_1$ is phenyl fused with an aromatic or non-aromatic cyclic ring of 5–7 members wherein said cyclic ring optionally contains up to two heteroatoms, independently selected from N, O and S;

and R$_2$ is H, NH(CH$_2$)$_n$-Ph or NH—C$_{1-6}$alkyl; and and R$_3$ is CO$_2$H, CONH$_2$, CN, NO$_2$, C$_{1-6}$alkylthio, SO$_2$—C$_{1-6}$alkyl, C$_{1-6}$alkoxy, SONH$_2$, CONHOH, NH$_2$, CHO, CH$_2$OH, CH$_2$NH$_2$, or CO$_2$R, wherein R is hydrogen or C$_{1-6}$alkyl.

2. A compound according to claim 1 wherein R$_1$ is phenyl optionally substituted with one or more substituents selected from the group consisting of halo, C$_{1-6}$alkoxy, C$_{1-6}$alkylthio, and phenyl; or R$_1$ is phenyl fused with an aromatic or non-aromatic cyclic ring of 5–7 members wherein said cyclic ring optionally contains up to two heteroatoms, independently selected from N, O and S.

3. A compound according to claim 1 wherein R$_2$ is other then hydrogen and is positioned ortho to the nitrogen of the pyridyl ring.

4. A compound according to claim 1 wherein R$_3$ is CO$_2$H, CONH$_2$, CONHOH, CH$_2$OH, CN or tetrazole.

5. A compound according to claim 1 wherein one of X$_1$ and X$_2$ is N or CR", and the other is NR" or CHR" wherein R" is hydrogen, C$_{1-6}$alkyl, or C$_{3-7}$cycloalkyl, provided that at least one of X$_1$ and X$_2$ is N or NR"; or one of one of X$_1$ and X$_2$ is N and the other is O.

6. A compound according to claim 5 wherein one of X$_1$ and X$_2$ is N and the other is NR".

7. A compound according to claim 1 wherein each R' is hydrogen.

8. A compound according to claim 1 selected from:

4-(4-Benzo[1,3]dioxol-5-yl-5-pyridin-2-yl-1H-imidazol-2-yl)phenol;

4-(4-Benzo[1,3]dioxol-5-yl-5-pyridin-2-yl-1H-imidazol-2-yl)-N-methyl-benzamide;

4-(4-Benzo[1,3]dioxol-5-yl-5-pyridin-2-yl-1H-imidazol-2-yl)-N-methoxy-benzamide;

2-{4Benzo[1,3]dioxol-5-yl-2-[4-(2H-tetrazol-5-yl)-phenyl]-1H-imidazol-5-yl}-pyridine;

[4-(4-Benzo[1,3]dioxol-5-yl-5-pyridin-2-yl-1H-imidazol-2-yl)-phenoxy]-acetic acid;

4-[4-(4-Fluoro-3-methoxyphenyl)-5-(6-methylpyridin-2-yl)-1H-imidazol-2-yl]-benzonitrile;

4-[4-(4-Fluoro-3-methoxyphenyl)-5-(6-methylpyridin-2-yl)-1H-imidazol-2-yl]-benzamide;

4-[4-(3-Fluoro-4-methoxyphenyl)-5-(6-methylpyridin-2-yl)-1H-imidazol-2-yl]benzonitrile;

4-[4-(3-Fluoro-4-methoxyphenyl)-5-(6-methylpyridin-2-yl)-1H-imidazol-2-yl]benzamide;

4-[4-Benzo[1,2,5]oxadiazol-5-yl-5-(6-methyl-pyridin-2-yl)-1H-imidazol-2-yl]benzonitrile;

4-[4-Benzo[1,2,5]oxadiazol-5-yl-5-(6-methylpyridin-2-yl)-1H-imidazol-2-yl]benzamide;

4-[4-(6-Methoxynaphthalen-2-yl)-5-(6-methylpyridin-2-yl)-1H-imidazol-2-yl]benzonitrile;

4-[4-(6-Methoxynaphthalen-2-yl)-5-(6-methylpyridin-2-yl)-1H-imidazol-2-yl]benzamide;

4-[4-Benzo[1,2,5]thiadiazol-5-yl-5-(6-methylpyridin-2-yl)-1H-imidazol-2-yl]benzonitrile;

4-[4-Benzo[1,2,5]thiadiazol-5-yl-5-(6-methylpyridin-2-yl)-1H-imidazol-2-yl]benzamide;

4-[4-Benzo[1,3]dioxol-5-yl-5-(6-methylpyridin-2-yl-1H-imidazol-2-yl]benzonitrile;

4-[4-Benzo[1,3]dioxol-5-yl-5-(6-methylpyridin-2-yl)-1H-imidazol-2-yl]benzamide;

6-[2-(4-Cyanophenyl)-5-(6-methylpyridin-2-yl)-1H-imidazole-4-yl]-quinoxaline; and 6-[2-(4-Carboxamidophenyl)-5-(6-methylpyridin-2-yl)-1H-imidazole-4-yl]-quinoxaline;

and pharmaceutically acceptable salts thereof.

9. A pharmaceutical composition comprising a compound according to claim 1, or a pharmaceutically acceptable salt thereof, and a pharmaceutically acceptable carrier or diluent.

* * * * *